US007618790B2

(12) United States Patent
Adriaenssens et al.

(10) Patent No.: US 7,618,790 B2
(45) Date of Patent: Nov. 17, 2009

(54) METHOD FOR NGF ASSAY FOR IN VITRO DIAGNOSIS OF BREAST CANCER AND THERAPEUTIC USE

(75) Inventors: Eric Adriaenssens, Saulzoir (FR); Geneviéve Choquet-Kastylevsky, Francheville (FR); Laurent Dolle, Villeneuve d'Ascq (FR); Ikram El-Yazidi Belkoura, Villeneuve d'Ascq (FR); Hubert Hondermarck, Villeneuve d'Ascq (FR)

(73) Assignees: Biomerieux, Marcy l'Etoile (FR); Universite des Sciences et Technologies de Lille, Villeneuve d'Ascq (FR)

( * ) Notice: Subject to any disclaimer, the term of this patent is extended or adjusted under 35 U.S.C. 154(b) by 0 days.

(21) Appl. No.: 10/530,568

(22) PCT Filed: Oct. 28, 2003

(86) PCT No.: PCT/FR03/03193

§ 371 (c)(1), (2), (4) Date: Apr. 7, 2005

(87) PCT Pub. No.: WO2004/040312

PCT Pub. Date: May 13, 2004

(65) Prior Publication Data

US 2006/0051818 A1 Mar. 9, 2006

(30) Foreign Application Priority Data

Oct. 28, 2002 (FR) .................................. 02 13428

(51) Int. Cl.
*G01N 33/574* (2006.01)

(52) U.S. Cl. ...................................... 435/7.23; 435/7.1

(58) Field of Classification Search ....................... None
See application file for complete search history.

(56) References Cited

U.S. PATENT DOCUMENTS

2003/0104364 A1* 6/2003 Billing-Medel et al. ........ 435/6

FOREIGN PATENT DOCUMENTS

| | | | |
|---|---|---|---|
| FR | 2 781 802 B1 | | 5/2001 |
| WO | WO 94/06935 A1 | | 3/1994 |
| WO | WO 95/08000 | | 3/1995 |
| WO | WO 97/38313 | * | 10/1997 |
| WO | WO 03/076942 A2 | | 9/2003 |

OTHER PUBLICATIONS

Sakamoto et al, Oncol Rep, 2001 8:973-980.*
Sakamoto et al., Oncol Rep, Sep.-Oct. 2001, 8:973-980.*
Varilek et al., Am J Physiol. 1995, 269:G445-G452.*
Picker et al., Blood, 1995, 86:1408-1419.*
Tockman et al, Cancer Res., 1992, 52:2711s-2718s).*
Slamon et al., Science vol. 235, Jan. 1987, pp. 177-182.*
Pica et al, AIDS, 1998, 12:2025-2029.*
Bigazzi et al, Clin Endocrinol, 1977, 6:105-112.*
Basuyau et al., "Standards, Options and Recommendations (SOR) for Tumor Markers in Breast Cancer," *Bull Cancer* 2000, No. 87, pp. 723-737 {2000}.
Springer, "Immunoreactive T and Tn Epitopes in Cancer Diagnosis, Prognosis, and Immunotherapy," *J. Mol. Med.*, No. 75, pp. 594-602 {1997}.
Gnjactic et al., "Accumulation of the p53 Protein Allows Recognition by Human CTL of a Wild-Type p53 Epitope Presented by Breast Carcinomas and Meloanomas," *Journal of Immunology.*, No. 160, pp. 328-333 {1998}.
Disis et al., "HER-2/neu Protein: A Target for Antigen-Specific Immunotherapy of Human Cancer," *Adv Cancer Res.*, No. 71, pp. 343-371 {1997}.
Jager et al., "Cancer-testis Antigens and ING1 Tumor Suppressor Gene Product are Breast Cancer Antigens: Characterization of Tissue-Specific ING1 Transcripts and a Homologue Gene," *Cancer Research*, No. 59; pp. 6197-6204 {1999}.
Jager et al., "Identification of a Tissue-Specific Putative Transcription Factor in Breast Tissue by Serological Screening of a Breast Cancer Library," *Cancer Research*, No. 61, pp. 2055-2061 {2001}.
Scanlan et al., "Challenges to the Development of Antigen-Specific Breast Cancer Vaccines," *Breast Cancer Research*, No. 3, pp. 95-98 {2001}.
Descamps et al., "Nerve Growth Factor is Mitogenic for Cancerous But Not Normal Human Breast Epithelial Cells," *The Journal of Biological Chemistry*, vol. 273, No. 27, pp. 16659-16662 {Jul. 3, 1998}.
Descamps et al., "Nerve Growth Factor Stimulates Proliferation and Survival of Human Breast Cancer Cells Through Two Distinct Signaling Pathways," *The Journal of Biological Chemistry*, vol. 276, No. 21, pp. 17864-17870 {May 25, 2001}.
Levi-Montalcini et al., "The Nerve Growth Factor 35 Years Later," *Science*, vol. 237, pp. 1154-1162 {1987}.
Torcia et al., "Nerve Growth Factor is an Autocrine Survival Factor for Memory B Lymphocytes," *Cell*, vol. 85, pp. 345-356 {May 3, 1996}.
Descamps et al., "Expression of Nerve Growth Factor Receptors and Their Prognostic Value in Human Breast Cancer," *Cancer Research*, No. 61, pp. 4337-4340 {Jun. 1, 2001}.

(Continued)

*Primary Examiner*—Misook Yu
*Assistant Examiner*—Mark Halvorson
(74) *Attorney, Agent, or Firm*—Oliff & Berridge, PLC

(57) ABSTRACT

The present invention concerns a method for the in vitro diagnosis of breast cancer which consists in determining the presence of NGF in a biological sample derived from a patient suspected of suffering from breast cancer. Said method may be used both in early diagnosis, screening, therapeutic follow-up and prognosis, and in the diagnosis of relapse in the case of breast cancer.

The present invention also concerns the use of an NGF binding partner or of an NGF inhibitor for preparing a medicinal product, said medicinal product being in particular useful for blocking tumor proliferation and remote dissemination in patients suffering from breast cancer.

8 Claims, 6 Drawing Sheets

OTHER PUBLICATIONS

Bonini et al., "Circulating Nerve Growth Factor Levels are Increased in Humans with Allergic Diseases and Asthma," *Proc. Natl. Acad. Sci. USA*, vol. 93, pp. 10955-10960 {Oct. 1996}.

Chevalier et al., "Biotin and Digoxigenin as Labels for Light and Electron Microscopy in Situ Hybridization Probes: Where Do We Stand?" *The Journal of Histochemistry & Cytochemistry*, vol. 45, No. 4, pp. 481-491 {1997}.

Patterson, "Mass Spectrometry and Proteomics," *Physiological Genomics* 2, pp. 59-65 {2000}.

Metezeau et al., *La Cytometrie En Flux*, vol. I, Medsi/McGraw-Hill Publications, pp. 21-74 {before Oct. 2003}.

*Intracellular Flow Cytometry,:Applied Reagents and Techniques*, pp. 1-21, BD Pharmingen {Oct. 2000}.

Hondermarck et al., "Early Changes in Protein Synthesis Induced by Basis Fibroblast Growth Factor, Nerve Growth Factor, and Epidermal Growth Factor in PC12 Pheochromocytoma Cells," *Proc. Natl. Acad. Sci. USA*, vol. 91, pp. 9377-9381 {Sep. 1994}.

Hattori et al., "Tumor Necrosis Factor Stimulates the Synthesis and Secretion of Biologically Active Nerve Growth Factor in Non-neuronal Cells," *The Journal of Biological Chemistry*, vol. 268, No. 4, pp. 2577-2582 {Feb. 5, 1993}.

Kumar et al., "The first Analogues of LNA (Locked Nucleic Acids): Phosphorothioate-LNA and 2'-Thio-LNA," *Bioorganic & Medicinal Chemistry Letters*, vol. 8, Issue 16, pp. 2219-2222 {Aug. 18, 1998}.

Egholm et al., "Peptide Nucleic Acids (PNA). Oligonucleotide Analogues with an Achiral Peptide Backbone," *J. Am. Chem. Soc.*, No. 114, pp. 1895-1897 {1992}.

Tapley et al., "K252a is a Selective Inhibitor of the Tyrosine Protein Kinase Activity of the *trk* Family of Oncogenes and Neurotrophin Receptors," *Oncogene*, No. 7, pp. 371-381 {1992}.

Dykxhoorn et al., "Killing the Messenger: Short RNAs that Silence Gene Expression," *Nature Review*, vol. 4, pp. 457-467 {Jun. 2003}.

Maleck et al., "Methods in Molecular Biology", No. 28, Ch. 36, Ed P.G. Issac, Humana Press, Inc., Totowa, NJ {1994}.

Cramer et al., "Nerve Growth Factor in Medullary Carcinoma of the Thyroid", Human Pathology, vol. 10, No. 6, pp. 731-736, Nov. 1979.

Gorctzki, M.D., R. A., "Nerve Growth Factor (NGF) Sensitizes Human Medullary Thyroid Carcinoma (hMTC) Cells for Cytostatic Therapy In Vitro", Surgery, pp. 1035-1042, Dec. 1987.

Moley et al., "Oncogene and Growth Factor Expression in MEN 2 and Related Tumors", Henry Ford Hosp. Med. Journal, vol. 40, No. 3 & 4, pp. 284-288, 1992.

Pica et al., "Autocrine Nerve Growth Factor is Essential for Cell Survival and Viral Maturation in HHV-8-Infected Primary Effusion Lymphoma Cells", Blood, vol. 95, No. 9, pp. 2905-2912, May 1, 2000.

Van Der Laan et al., "Expression of Growth Factors and Growth Factor Receptors in Normal and Tumorous Human Thyroid Tissues", Thyroid, vol. 5, No. 1, pp. 67-73, 1995.

* cited by examiner

Fig 1A
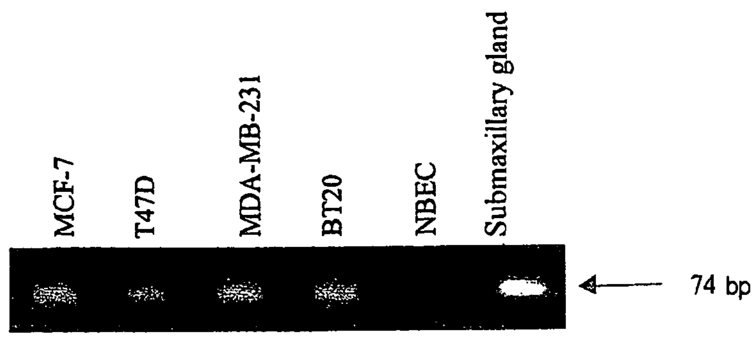
Fig 1B
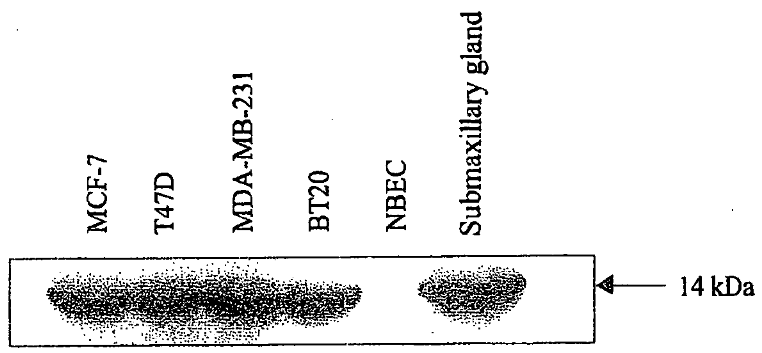
Fig 1C
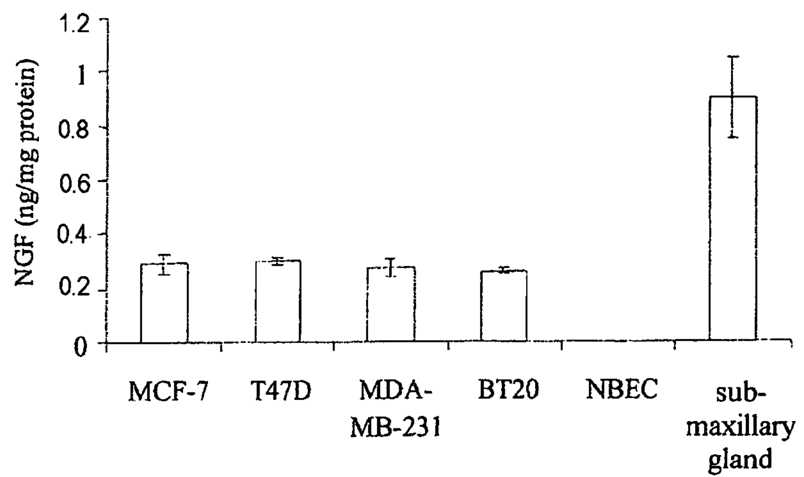
Figure 1

Fig 2A
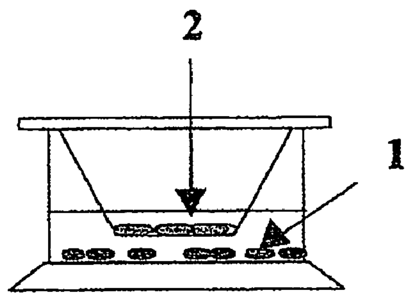
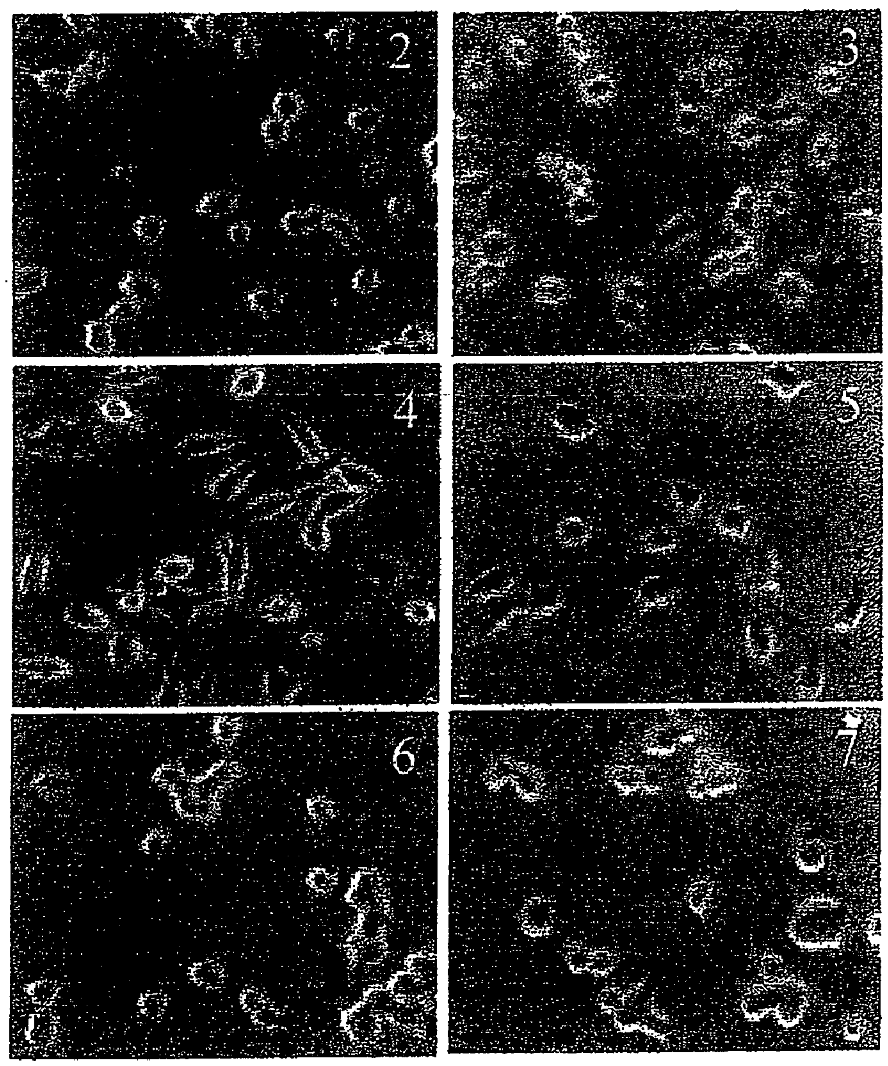
Fig 2B
Figure 2

Fig 4A
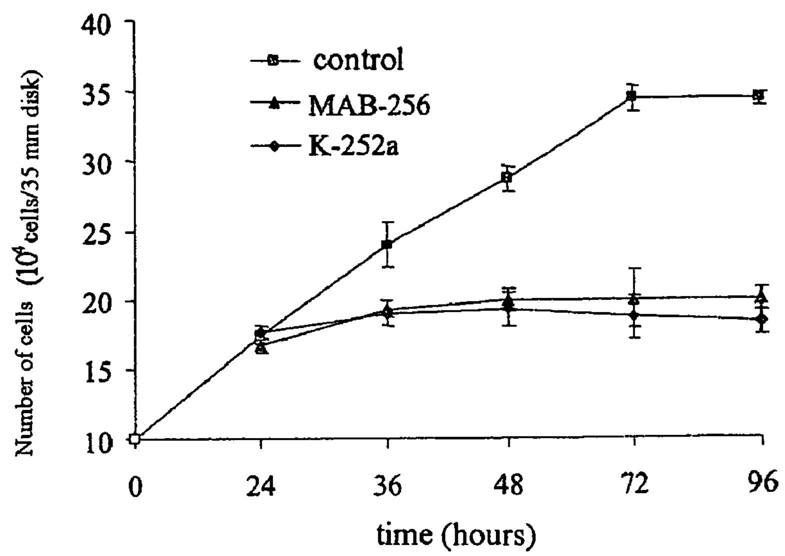
Fig 4B
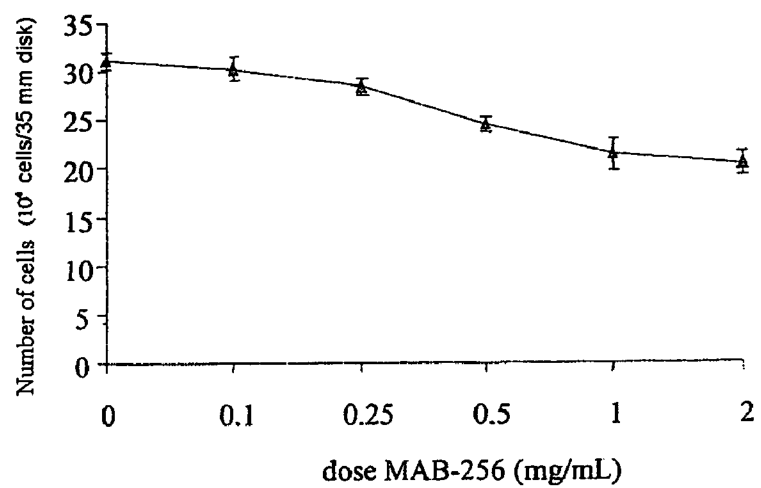
Fig 4C
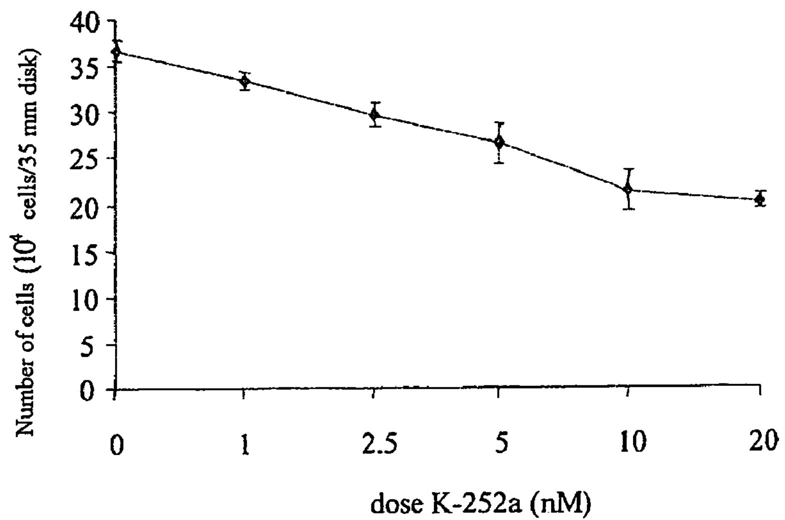
Figure 4

METHOD FOR NGF ASSAY FOR IN VITRO DIAGNOSIS OF BREAST CANCER AND THERAPEUTIC USE

The present invention relates to the field of cancerology. More particularly, the present invention relates to a method for the diagnosis of breast cancer in a human patient by determining the presence of nerve growth factor (NGF) in a biological sample derived from this patient, it being possible for said method to be used both in early diagnosis, screening, therapeutic-follow up and prognosis, and in the diagnosis of relapse in the case of breast cancer. In addition, due to the ability of breast cancer cells to produce NGF, the present invention also relates to therapy.

In women, breast cancer is the primary cause of mortality due to cancer in industrialized countries. It is estimated that the minimum size of a tumor that can be detected by mammography is 1 cm. Breast cancers develop slowly. However, this small tumor has an evolutive past of 8 years, on average, at the time of diagnosis. The etiology of breast cancer is not well defined. Familial predispositions have been demonstrated. Age is the most important risk factor. Thus, the risk increases by 0.5% per year of age in countries in the west. Other risk factors are known, such as the number of pregnancies and the age of the first pregnancy, breast-feeding, the age at puberty and at the menopause, estrogenic treatments after the menopause has occurred, stress and nutrition.

The test available and used in mass screening for breast cancer is an imaging technique: mammography. By virtue of this technique, mortality due to breast cancer has greatly decreased (30% reduction in mortality), which underlines the importance of tumor screening in terms of public health. However, the screening techniques suffer from a certain number of handicaps. Mammography requires high-performance material and qualified personnel, which is expensive in the case of mass screening.

In clinical practice, the characterization of a tumor in terms of malignancy is carried out, after it has been discovered, by histological methods in specialized laboratories. A set of parameters such as the size of the tumor, its histopathological grade, and the inflammation associated with the invasion of the lymphoids are used to decide upon the therapy and to estimate the prognosis for the disease.

Markers which make it possible to distinguish between tumor cells and normal cells have been sought and studied for years for breast cancer. They would make it possible to diagnose the disease early, to establish the prognosis thereof and the sensitivity thereof to treatment, and to monitor the evolution thereof. Up until now, the candidate markers that have been identified and studied have been oncogenes, tissue markers and markers associated with angiogenesis or with the metastatic capacities of the tumor. Currently, the breast cancer markers that have been identified are used mainly for therapeutic follow-up. No validated biological test exists for the early diagnosis or for the screening of breast cancer. Only the detection of oestrogen receptors on the tumor tissue makes it possible to determine whether the tumors will or will not be hormone-sensitive.

A limited number of antigenic markers, in particular CA 15-3 (Basuyau, J. P., M. P. Blanc-Vincent, J. M. Bidart, A. Daver, L. Deneux, N. Eche, G. Gory-Delabaere, M. F. Pichon, and J. M. Riedinger. 2000. [Standards, Options and Recommendations (SOR) for tumor markers in breast cancer. SOR Working Group]. Bull Cancer. 87:723-37) has been identified in the case of cancerous mammary cells. This marker is used in common practice for the follow-up of patients, in particular for the detection of relapse, but, due to its low sensitivity, it is not proposed in a screening or diagnostic test.

For several years, studies relating to breast cancer-associated antigens have been developed not in order to search for markers, but to search for targets for immunotherapy. These range from the demonstration of humoral immunity against T/Tn antigens (Springer, G. F. 1997. Immunoreactive T and Tn epitopes in cancer diagnosis, prognosis, and immunotherapy. J Mol Med. 75:594-604), to the more recent discovery of antibodies and of T-cell responses directed against p53 (Gnjatic, S., Z. Cai, M. Viguier, S. Chouaib, J. G. Guillet, and J. Choppin. 1998. Accumulation of the p53 protein allows recognition by human CTL of a wild-type p53 epitope presented by breast carcinomas and melanomas. J Immunol. 160:328-33) and HER-2/neu (Disis, M. L., and M. A. Cheever. 1997. HER-2/neu protein: a target for antigen-specific immunotherapy of human cancer. Adv Cancer Res. 71:343-71).

More recently, a series of novel potential antigens has been demonstrated by the SEREX (serological expression cloning) approach, based on the construction of tumor cell cDNA libraries and screening with the autologous serum. A serological breast cancer library screening thus made it possible to demonstrate the ING1 antigen (Jager, D., E. Stockert, M. J. Scanlan, A. O. Gure, E. Jager, A. Knuth, L. J. Old, and Y. T. Chen. 1999. Cancer-testis antigens and ING1 tumor suppressor gene product are breast cancer antigens: characterization of tissue-specific ING1 transcripts and a homologue gene. Cancer Res. 59:6197-204), followed by a novel differentiation antigen NY-BR-1, that is expressed, according to the authors, in 80% of breast cancers and induces the production of IgG antibodies in the patients (Jager, D., E. Stockert, A. O. Gure, M. J. Scanlan, J. Karbach, E. Jager, A. Knuth, L. H. Old, and Y. T. Chen. 2001. Identification of a tissue-specific putative transcription factor in breast tissue by serological screening of a breast cancer library. Cancer Res. 61:2055-61). This type of approach, which has mainly been used to search for targets that can potentially be used to develop vaccines, does not exclude, a priori, the antigens present in the normal tissue (this is the case of NY-BR-1), nor those recognized by a limited number of patient sera (2/14 for ING1); they are not therefore exploitable for a screening or early diagnosis strategy. Using the same approach, other antigens that induce a humoral immune response in patients have been noted, such as NY-BR-62, NY-BR-85 and the D52 protein. These antigens are thought to be overexpressed, respectively, in 60%, 90% and 60% of breast cancers (Scanlan, M. J., and D. Jager. 2001. Challenges to the development of antigen-specific breast cancer vaccines. Breast Cancer Res. 3:95-8).

The molecular phenomena that result in the development of a breast cancer involve modifications of the structure and of the expression of oncogenes (such as ras) and of tumor suppressor genes such as p53. In most breast cancers, tumor cell growth is dependent on oestrogenic hormones (estradiol and progesterone) and on growth factors that control proliferation, migration and apoptosis. These growth factors either stimulate or inhibit the proliferation, migration and differentiation of the tumor cells in such a way as to act in concert so as to favor the growth of the cancer and the metastases. For example, insulin-type growth factors, transforming growth factor $\alpha$ (TGF-$\alpha$) and fibroblast growth factors (FGFs) can all stimulate the proliferation of breast cancer cells, whereas mammary derived growth factor inhibitor (MDGI) and transforming growth factor $\beta$ (TGF-$\beta$) inhibit their growth.

S. Descamps et al. have demonstrated that the growth factor NGF, which was the first neurotrophic factor discovered, when added in vitro to cell lines in culture (exogenous NGF), is potentially capable of activating both the survival and proliferation of breast cancer cells (1998, J. Biol. Chem., 273 (27), 16659-16662 and 2001, J. Biol. Chem., 276(21), 17864-17870).

NGF was initially isolated for its ability to stimulate both the survival and the differentiation of peripheral neurons, later becoming the archetypal element of the neurotrophic polypeptides family (Levi-Montalcini, R., 1987, Science, 4237, 1154-1162). A major biological function of NGF is the maintenance and survival of post-mitotic neurons, which makes it an important candidate for the treatment of neurodegenerative diseases. Besides its role in the development and maintenance of neuronal cells, NGF also has significant effects on non-neuronal cells. Thus, for example, it is an autocrine survival factor for B lymphocytes (Torcia, M., et al., 1996, Cell, 85, 345-356).

NGF generates intracellular signals by interaction with two classes of membrane receptor: the proto-oncogenic product of TrkA $p140^{trkA}$, which has intrinsic tyrosine kinase activity, and a second receptor, $p75^{NTR}$, which belongs to the tumor necrosis factor (TNF) receptor family. In breast cancer cells, two distinct NGF-activated signaling pathways exist. The mitogenic effect requires the $p140^{trkA}$ receptor and the MAP kinase cascade, while the anti-apoptotic effect depends on the $p75^{NTR}$ receptor and on the downstream activation of the factor NF-κB (S. Descamps, et al., 2001, above). Thus, for the diagnosis of breast cancer, some authors have turned to the detection of NGF receptors, such as for example in patent application WO 94/06935, which describes a method for the diagnosis of a precancerous or cancerous state in a patient by assaying the amount of p75 receptor.

The powerful biological effect of NGF on breast cancer cells also raises the question of its distribution in the mammary gland and of its origin. It is generally thought that NGF is produced by sympathetic and sensory innervation targets, although it has not been found in the bloodstream (Bonini, S. et al; 1996, Proc., Natl. Acad. Sci. USA, 93, 10955-10960).

The applicant has now demonstrated, surprisingly, that breast cancer cells themselves produce NGF, whereas corresponding normal mammary epithelial cells do not produce any, such that NGF can be used as a tumor marker or else as a therapeutic target.

Thus, a first subject of the present invention is a method for the diagnosis of breast cancer by determining the presence of NGF in biological samples derived from patients suspected of suffering from breast cancer.

The method of the invention therefore makes it possible to diagnose breast cancer by means of a simple test consisting in searching for the presence of NGF in a biological sample taken from a patient. The applicant has shown, unexpectedly, that cancer cells produce NGF, whereas the corresponding non-cancerous cells are incapable of this, as will be demonstrated in greater detail hereinafter. Thus, determination of the presence of NGF in the sample makes it possible to conclude that there is a pathology, an absence of NGF making it possible to conclude that there is no pathology.

The expression "determination of the presence of NGF" is intended to mean either the direct detection of NGF, or the culturing of NGF-sensitive cells, or the detection of NGF mRNA in the biological sample, or any other method for determining the presence of a protein in a sample, known to those skilled in the art.

The determination of the presence of NGF by direct detection of NGF constitutes a particular embodiment of the invention.

The expression "direct detection of NGF" is intended to mean the demonstration of NGF itself in the biological sample.

The direct detection of NGF in the biological sample can be carried out by any means known to those skilled in the art, for instance by means of an immunoassay or by mass spectrometry, which constitutes a particular embodiment of the invention.

The immunoassay can be any assay widely known to those skilled in the art that involves immunoreactions, i.e. reactions between NGF and a specific NGF binding partner.

The specific NGF binding partners are any partner capable of binding to NGF. By way of example, mention may be made of antibodies, antibody fractions, receptors and any other protein capable of binding to NGF.

The binding-partner antibodies are either polyclonal antibodies or monoclonal antibodies.

The polyclonal antibodies can be obtained by immunization of an animal with NGF, followed by recovery of the desired antibodies in purified form, by taking the serum from said animal, and separation of said antibodies from the other serum constituents, in particular by affinity chromatography on a column to which is attached an antigen that is specifically recognized by the antibodies, in particular NGF.

The monoclonal antibodies can be obtained by the hybridoma technique, the general principle of which is recalled below.

Firstly, an animal, generally a mouse (or cells in culture in the case of in vitro immunizations), is immunized with NGF, the B lymphocytes of said animal then being capable of producing antibodies against said antigen. These antibody-producing lymphocytes are then fused with "immortal" myeloma cells (murine cells in the example) so as to produce hybridomas. The cells capable of producing a specific antibody and of multiplying indefinitely are then selected from the heterogeneous mixture of the cells thus obtained. Each hybridoma is multiplied in the form of a clone, each resulting in the production of a monoclonal antibody whose properties of recognition with respect to the tumor antigen of interest may be tested, for example, by ELISA, by one- or two-dimensional immunoblot, by immunofluorescence, or by means of a biosensor. The monoclonal antibodies thus selected are subsequently purified, in particular according to the affinity chromatography technique described above.

Examples of anti-NGF antibodies are known and are available, in particular in the R&D Systems catalogue or the Santa Cruz catalogue.

The specific NGF binding partners may be labeled in order to reveal the NGF/binding partner binding when the binding partner is used as a detection reagent, and therefore for the direct detection of NGF in the biological sample.

The expression "labeling of the binding partners" is intended to mean the attachment of a label capable of directly or indirectly generating a detectable signal. A non limiting list of these labels consists of:

- enzymes which produce a signal that can be detected, for example by colorimetry, fluorescence or luminescence, such as horseradish peroxidase, alkaline phosphatase, α-galactosidase or glucose-6-phosphate dehydrogenase,
- chromophores such as fluorescent, luminescent or dye compounds,
- radioactive molecules such as $^{32}P$, $^{35}S$ or $^{125}I$, and
- fluorescent molecules such as alexa or phycocyanins.

Indirect systems can also be used, for instance ligands capable of reacting with an anti-ligand. Ligand/anti-ligand couples are well known to those skilled in the art, which is the case for example of the following couples: biotin/streptavidin, haptene/antibody, antigen/antibody, peptide/antibody, sugar/lectin, polynucleotide/sequence complementary to the polynucleotide. In this case, it is the ligand that bears the binding agent. The anti-ligand may be directly detectable by means of the labels described in the above paragraph or may itself be detectable by means of a ligand/anti-ligand.

These indirect detection systems may result, under certain conditions, in an amplification of the signal. This signal amplification technique is well known to those skilled in the art, and reference may be made to the prior patent applications FR 98/10084 or WO-A-95/08000 by the applicant or to the article J. Histochem. Cytochem. 45:481-491, 1997.

According to the type of labeling of the conjugate used, those skilled in the art will add reagents for visualizing the labeling.

By way of example of immunoassays as defined above, mention may be made of "sandwich" methods such as ELISA, IRMA and RIA, "competition" methods, and direct immunodetection methods such as immunohistochemistry, immunocytochemistry, Western blotting and dot-blotting.

Mass spectrometry can also be used for the direct detection of NGF in the biological sample. The principle of spectrometry is widely known to those skilled in the art and is described, for example, in S. Patterson, 2000, Mass spectrometry and proteomics. Physiological Genomics 2, 59-65.

To do this, the biological sample, which may or may not have been pretreated, is passed through a mass spectrometer and the spectrum obtained is compared with that of NGF. An example of pretreatment of the sample consists in passing it over an immunocapture support containing one of the NGF binding partners, for example an antibody directed against NGF.

The biological sample used for the direct detection of NGF, liable to contain NGF as such, may consist of biological fluid or a tissue originating from the biopsy of the tumor or of the metastases of the patient under consideration.

By way of biological fluid, mention may be made of blood, bone marrow, milk, cerebrospinal fluid, urine and effusions.

For the detection of NGF, the biological fluid, which constitutes a particular embodiment of the invention, may require a particular treatment. Specifically, the biological fluid may contain the NGF as such, or else it may contain circulating tumor cells which contain NGF, and possibly circulating tumor cells which are capable of secreting the NGF.

Thus, according to one embodiment of the invention, the biological fluid is pretreated in order to isolate the circulating tumor cells contained in said fluid.

The expression "to isolate the circulating tumor cells" is intended to mean to obtain a cell fraction enriched with circulating tumor cells.

The treatment of the fluid in order to isolate the circulating tumor cells can be carried out by cell sorting in a flow cytometer, by enrichment on Ficoll, by enrichment with magnetic beads coated with specific antibodies, or by any other method of specific enrichment known to those skilled in the art.

In the case of blood or of bone marrow as biological fluid, the circulating tumor cells can be isolated by means of a technique consisting of cell separation on Ficoll associated with depletion of the blood cells using anti-CD45 antibodies coupled to magnetic beads (Dynal Biotech ASA, Norway).

The direct detection of NGF can then be carried out directly using circulating tumor cells isolated from the biological fluid, for example by immunocytochemical labeling of these cells with an anti-NGF antibody, after having deposited the circulating tumor cell onto a slide by cytospin. The direct detection of NGF can also be carried out directly in the circulating tumor cells using the flow cytometry method as described in Métézeau P, Ronot X, Le Noan-Merdrignac G, Ratinaud M H, La cytométrie en flux pour l'étude de la cellule normale ou pathologique [Flow cytometry for studying normal or pathological cells] (Volume I), Medsi-MacGrawhill publishers.

Under these conditions, said circulating cells can be treated under conditions that block the NGF inside said cells. Such a treatment is described, for example, in Intracellular Flow Cytometry, Applied reagents and Techniques, pp 1-21, BD Pharmingen.

The detection of NGF is then carried out after having made the cell membrane permeable so as to cause the specific NGF binding partners to enter.

The direct detection of NGF using circulating cells can also be carried out by means of the method described in patent application WO 03/076942 filed by one of the applicants.

The direct detection of NGF in tumor cells can also be carried out in the culture medium of said cells after having cultured them under conditions such that they secrete NGF.

These culture conditions are conventional conditions such as 37° C. in a humid atmosphere and at 5% $CO_2$.

When the biological sample to be tested is tissue originating from the biopsy of the tumor or of the metastases of the patient, which constitutes a particular embodiment of the invention, the direct detection of NGF is carried out directly on the sections obtained, without pretreatment of said tissue.

Another method for detecting the presence of NGF consists in culturing NGF-sensitive cells in the presence of the biological sample, which constitutes a particular embodiment of the invention.

In this case, the detection of the presence of NGF in a biological sample is demonstrated by means of the reaction of the NGF-sensitive cells.

The term "NGF-sensitive cells" is intended to mean any cell that is stimulated in the presence of NGF (growth, apoptosis, etc).

By way of NGF-sensitive cells, mention may be made of PC12 pheochromocytoma cells (Hondermarck H. et al., 1994, Proc. Natl. Acad. Sci., 91:9377-81) and embryonic cells of neuronal origin (Hattori A., et al., 1994, J. Biol. Chem., 268:2577-2582).

The biological sample that can be used for detecting the presence of NGF by culturing NGF-sensitive cells may be any sample as described above.

Thus, the biological sample may consist of biological fluid, where appropriate pretreated in order to isolate the circulating tumor cells, which can themselves then be cultured under conditions such that they secrete NGF, as described above.

Another method for detecting the presence of NGF in the biological samples consists in detecting the NGF mRNA in said sample, which constitutes another embodiment of the invention.

The detection of mRNA in a liquid sample is widely known to those skilled in the art.

It may, for example, be carried out by means of hybridization reactions between the target mRNA and a nucleic acid capable of binding with the target mRNA.

The term "nucleic acid" is intended to mean oligonucleotides, deoxyribonucleic acids and ribonucleic acids, and also derivatives thereof.

The term "oligonucleotide" denotes a chain of at least 2 natural or modified nucleotides (deoxyribonucleotides or ribonucleotides, or both) capable of hybridizing, under appropriate hybridization conditions, with an oligonucleotide that is at least partially complementary. The term "modified nucleotide" is intended to mean, for example, a nucleotide containing a modified base and/or containing a modification at the level of the internucleotide bond and/or at the level of the backbone. By way of example of modified bases, mention may be made of inosine, methyl-5-deoxycytidine, dimethylamino-5-deoxyuridine, diamino-2,6-purine and bromo-5-deoxyuridine. By way of illustration of a modified internucleotide bond, mention may be made of phosphorothioate, N-alkylphosphoramidate, alkylphosphonate and alkylphosphodiester bonds. Alpha-oligonucleotides such as those described in FR-A-2 607 507, LNAs such as phosphorothioate-LNAs and 2'-thio-LNAs described in Bioorganic & Medicinal Chemistry Letters, Volume 8, Issue 16, Aug. 18, 1998, pages 2219-2222, and the PNAs which are the subject of the article by M. Egholm et al., J. Am. Chem. Soc. (1992), 114, 1895-1897, are examples of oligonucleotides consisting of nucleotides whose backbone is modified.

The hybridization reactions can be visualized by labeling of the binding nucleic acids, as illustrated above.

Before hybridization with the binding nucleic acid, the target mRNA can be extracted by methods known to those skilled in the art, and then optionally amplified, for instance by RT-PCR or by NASBA (Maleck, L., et al., 1994, Methods in Molecular Biology, 28, Ch 36, Ed P. G. Isaac, Humana Press, Inc., Totowa, N.J.).

The biological sample that can be used for detecting the presence of NGF by detecting NGF mRNA may be any sample as described above.

Thus, the biological sample may consist of tissue derived from a tumor biopsy or a metastasis biopsy, or else of biological fluid, where appropriate pretreated in order to isolate the circulating tumor cells, as described above.

The method of the invention can be used both for early diagnosis and for screening, therapeutic follow-up, prognosis and diagnosis of relapse in the case of breast cancer, since only the cancer cells produce NGF and this production depends on the grade of the cancer.

Thus, another subject of the invention consists of the use of the method of the invention in early diagnosis, screening, therapeutic follow-up, prognosis and the diagnosis of relapse in the case of breast cancer.

Besides the role as a tumor marker, NGF may also have a role as a therapeutic target. In fact, due to the ability of breast cancer cells to produce NGF, while the normal cells do not produce it, the tumor proliferation and the remote dissemination of the breast cancer cells can be blocked by means of an NGF binding partner capable of blocking the cell proliferation, or by means of an NGF inhibitor.

The NGF binding partners and the NGF inhibitors can therefore be used as medicinal products.

Thus, a subject of the present invention is also the use of an NGF binding partner or of an NGF inhibitor for preparing a medicinal product, it being understood that, in the case of cancer, the NGF binding partners are not receptors for the NGF or active fragments of these receptors.

According to a particular embodiment of the invention, said medicinal product is useful for blocking tumor proliferation and remote dissemination in patients suffering from breast cancer.

The pharmaceutical compositions comprising, as active principle, at least one NGF binding partner or one NGF inhibitor, optionally combined with a pharmaceutically acceptable excipient, are also included in the invention, it being understood that, in the case of cancer, the NGF binding partners are not receptors for NGF or active fragments of these receptors.

The pharmaceutical compositions that are useful against breast cancer comprise, as active principle, at least one NGF binding partner capable of blocking tumor cell proliferation, or an NGF inhibitor.

The specific NGF binding partners that are suitable as an active principle are in particular as defined above in the immunoassays, and can be any other partner known to those skilled in the art capable of blocking tumor proliferation. According to a particular embodiment, the specific partner capable of blocking breast cancer cell proliferation is an anti-NGF antibody.

The term “NGF inhibitor” is intended to mean direct inhibitors of NGF, i.e. inhibitors that block the biological activity of the protein, inhibitors of the exocytosis pathways for NGF, inhibitors of the NGF mRNA, and inhibitors of the gene encoding NGF.

As a direct inhibitor of NGF, mention may be made of the inhibitor K-252a (Tapley, P., et al., 1992, Oncogene 7, 371-381).

Inhibitors of the exocytosis pathways for proteins, and in particular for NGF, are widely known to those skilled in the art.

As an NGF mRNA inhibitor, a synthetic fragment of this mRNA may be used. Specifically, interfering RNA technology is based on the use of a double-stranded RNA oligonucleotide corresponding to a short sequence of the cellular mRNA to be inhibited. This duplex oligonucleotide (possibly introduced into a plasmid), after entering into the cell, is processed by the Dicer/Risc enzymatic system, which will result in degradation of the corresponding cellular mRNA (Dykxhoorn D et al., 2003, Nature Review, Vol. 4, p 457-467).

As an inhibitor of the gene encoding NGF, mention may be made of an NGF antisense oligonucleotide. This oligonucleotide can be readily prepared by those skilled in the art.

In order to target the therapeutic action of the NGF binding partners or of the various inhibitors, they can be placed under conditions such that they specifically enter the cells of interest, such as the tumor cells, which constitutes another embodiment of the invention.

To this effect, they can, for example, be attached to a partner which allows such an entry, for instance a carrier molecule, a polymer such as the polymers used in gene therapy, or else a viral vector such as adenoviruses and poxviruses, also used in gene therapy.

For example, in the case of breast cancer, the carrier molecule may be an anti-MUC1 antibody or an anti-epithelial cell antibody, or alternatively an anti-HER-2/neu antibody.

Preferably, when the pharmaceutical composition comprises, as active principle, an NGF binding partner or an NGF inhibitor such as a direct inhibitor or an inhibitor of the exocytosis pathways for NGF, the latter are placed under conditions such that they specifically enter the tumor cells of interest, NGF mRNA inhibitors and inhibitors of the gene encoding NGF having the ability to naturally enter said cells.

The amount and nature of the excipient can be readily determined by those skilled in the art. They are chosen according to the pharmaceutical form and the method of administration desired.

In the pharmaceutical compositions of the invention for oral, sublingual, subcutaneous, intramuscular, intratumor, intravenous, topical, local, intratracheal, intranasal, transdermal, rectal, intraocular or intraauricular administration, said active principle can be administered in a unit form of administration.

The unit forms of administration may, for example, be tablets, gelatin capsules, granules, powders, injectable oral solutions or suspensions, transdermal patches, sublingual, buccal, intratracheal, intraocular, intranasal or intraauricular administration forms, forms of administration by inhalation, topical, transdermal, subcutaneous, intramuscular, intratumor or intravenous administration forms, rectal administration forms, or implants. For topical administration, creams, gels, ointments, lotions or eye lotions can be envisioned.

These pharmaceutical forms are prepared according to the usual methods in the fields under consideration.

Said unit forms contain a dosage so as to allow daily administration of 0.001 to 10 mg of active principle per kg of body weight, according to the pharmaceutical form.

There may be particular cases where higher or lower dosages are appropriate; such dosages do not depart from the context of the invention. According to the usual practice, the dose appropriate for each patient is determined by the physician according to the method of administration and the weight and response of the patient.

According to another embodiment, the present invention also relates to a method of treating breast cancer which comprises the administration, to a patient, of an effective dose of an NGF binding partner or of an NGF inhibitor.

The invention will be understood more clearly from the following examples, given by way of nonlimiting illustration, and also from the attached FIGS. 1 to 5, in which:

FIG. 1 concerns representations in the form of graphs relating to the demonstration of the expression of NGF in cancer cells, in which:

FIG. 1A represents an electrophoresis gel demonstrating, after RT-PCR, the secretion of NGF by MCF-7, T47D, MDA-MB-231 and BT20 cancer cells and by submaxillary gland cells as a control, and also the absence of such a secretion by NBEC normal cells (Normal Breast Epithelial Cells), FIG. 1B represents an electrophoresis gel demonstrating, after immunoblotting, the secretion of NGF by MCF-7, T47D, MDA-MB-231 and BT20 cancer cells and by submaxillary gland cells, and also the absence of such a secretion by NBEC cells, and FIG. 1C is a graph giving the amount of NGF secreted as a function of the cells assayed by ELISA, i.e. MCF-7, T47D, MDA-MB-231 and BT20 cancer cells, submaxillary gland cells and NBEC cells, FIG. 2 concerns representations regarding the coculture of cancer cells and of NGF-sensitive cells, in which:

FIG. 2A represents the experimental scheme for coculturing of the PC12 cells (1) that develop in the presence of NGF and of cancer cells (2), and FIG. 2B consists of photographs representing the culturing of PC12 cells as a control (photograph 2), the differentiation of PC12 cells under the influence of NGF (photograph 3), the coculturing of NGF-sensitive cells in the presence of MCF-7 cancer cells (photograph 4), the culturing of MCF-7 cancer cells in the presence of an anti-NGF antibody (photograph 5), the culturing of MCF-7 cancer cells in the presence of the inhibitor K252a (photograph 6), and the culturing of NBEC normal mammary cells (photograph 7), FIG. 3 represents photographs of immunocytochemistry demonstrating the expression of NGF by immunodetection in tissue derived from biopsy, in which photographs A and B relate to the normal tissue, respectively with or without NGF labeling, photographs C to F relate to the cancerous tissue, photographs C and E relate to the sections without NGF labeling (negative control) and photographs D and F relate to the sections with NGF labeling, FIG. 4 relates to graphs demonstrating the influence, on cell growth, of a binding partner capable of blocking breast cancer cell proliferation, in which:

FIG. 4A represents a graph showing the growth of MCF-7 cells as number of cells ($10^4$ cells/35 mm disk), either without agent for blocking tumor proliferation, as a control, or in the presence of the anti-NGF antibody MAB-256, or in the presence of the inhibitor K-252a, and FIGS. 4B and 4C represent graphs giving the number of MCF-7 cells as a function of the dose of the MAB-256 antibody (FIG. 4B) or of the dose of the inhibitor K-252a (FIG. 4C), and FIG. 5 gives graphs demonstrating the influence of an anti-NGF antibody, as a function of time, on the tumor volume (FIG. 5A), on the tumor mass (FIG. 5B) and on the number of liver metastases (FIG. 5C) of mouse breast cancer cells.

EXAMPLE 1

Demonstration of the Expression of NGF in Breast Cancer Cells by RT-PCR 1.1 Cells Tested Four human breast cancer cell lines were tested, i.e. MCF-7, T47D, MDA-MB-231 and BT20 cells, obtained from the ATCC collection (Rockville, Md.) under the numbers HTB-22, HTB-133, HTB-26 and HBT-29, respectively.

These cells were maintained in minimum essential medium (Earle's salts, BioWhittaker, Belgium) supplemented with 20 mM Hepes, 2 g/l of sodium bicarbonate, 2 mM of L-glutamine, 10% of fetal calf serum (FCS), 100 units/ml of penicillin-streptomycin, 50 μg/ml of gentamycin, 1% of non essential amino acids and 5 μg/ml of insulin.

By way of comparison, normal breast epithelial cells (NBEC) obtained from the Department of Plastic Surgery of the Medical University of Lille (Professor Pellerin, France), which were cultured in DMEM/F12 (1/1) medium (BioWhittaker) containing 5% of FCS, 10 IU/ml of insulin, 5 μM of cortisol, 2 ng/ml of EGF, 100 ng/ml of cholera toxin, 100 ng/ml of penicillin and 45 μg/lm of gentamycin (medium B1), were tested. When the cells approached confluency, they were placed in the same medium, except that the calcium concentration was decreased to 20 μM.

Human submaxillary gland cells, obtained from hospital dissection residues, were also used as a known source of NGF.

1.2 RT-PCR

The total RNA was isolated from the cancer cell lines, from the NBEC cells and from the human submaxillary gland (20 mg by weight) cells using the Rneasy mini kit (Qiagen, France). The submaxillary gland was ruptured and homogenized using a Rotor-Stator homogenizer (Bribolyser, Hybaid).

The amount of RNA extracted was quantified by measuring the absorbence at 260 nm, and the purity of the RNA was investigated by means of the ratio of absorbence at 260 nm to absorbence at 280 nm. The absence of degradation of the RNA was confirmed by electrophoresis of the RNA on a 1.5% agarose gel containing ethidium bromide.

The reverse transcription (RT) was carried out by adding a reaction mixture containing 2 g of purified total mRNA, 1× reaction buffer, 10 mM of DTT, 400 mM of dNTP for each, 2.5 M of oligo(dT), 40 units of Rnasin and 200 units of Moloney murine leukemia virus reverse transcriptase, with a total reaction volume of 25 μl. All the reactions were incubated at 37° C. for 1 h, and then inactivated at 95° C. for 5 min.

The PCR was carried out on the cDNAs after RT or on the RNA samples without the RT step for the negative controls, as follows:

5 μl of PCR buffer (200 mM of Tris-HCl, pH 8.4, 500 mM KCl), 10 μl of 15 mM $MgCl_2$, 1 ml of 10 mM dNTP mix, 1 μl of cDNA or of total mRNA (for the negative control), 1 μl of 50 mM of the probes for the ngf gene indicated below, 1 μl of 2.5 units/μl of Taq DNA polymerase and water up to a total volume of 50 μl were added to PCR tubes.

```
Sense probe:        5'-GACAGTGTCAGCGTGTGGGTT-3'
                    (SEQ ID NO: 1)

Antisense probe:    5'-CCCAACACCATCACCTCCTT-3'.
                    (SEQ ID NO: 2)
```

The PCR conditions were as follows: after treatment at 95° C. for 3 min in order to denature the cDNA, 30 cycles consisting of 94° C. for 1 min, 57° C. for 2 min and 72° C. for 3 min were performed. The PCR tubes were then incubated for a further 10 min at 72° C. for extension of the cDNA fragments after the final cycle.

The visualization of the amplified material under UV-light by means of ethidium bromide staining after agarose gel electrophoresis is represented in FIG. 1A. This figure shows a 74 bp ngf transcription product for the cancerous epithelial cells and the submaxillary gland cells (positive control), whereas this product is not detected for the NBEC cells.

This test therefore makes it possible to demonstrate that the cancerous cells secrete NGF, whereas the corresponding non-cancerous epithelial cells do not secrete it.

EXAMPLE 2

Demonstration of the Expression of NGF in Breast Cancer Cells by Immunoblotting 2.1 Cells Tested The cells tested are those indicated in point 1.1. above.

2.2 Immunoblotting

Subconfluent cells, cultured as indicated in point 1.1 above, were rinsed and placed in a serum-free medium containing fibronectin and transferrin for 24 h. After the cells had been deprived of nutrients, they were collected by scraping in a PBS buffer (phosphate buffered saline solution) and were subjected to centrifugation (1000×g, 5 min).

The pellet was treated with lysis buffer (100% SDS, 0.5% of β-mercaptoethanol, 0.5 M Tris HCl, pH 6.8, 25% glycerol, 0.5%) and the mixture was boiled for 5 min at 100° C.

After centrifugation (1000×g, 5 min) the proteins in the supernatants were investigated using Bio Rad protein determination assays.

The lysates originating from each cell line and from the submaxillary gland were subjected to SDS-PAGE and were transferred onto a nitrocellulose membrane by electroblotting (200 mA, 45 min).

Each membrane was then tested with an anti-NGF rabbit polyclonal antibody (sc-548, Santa Cruz Biotechnology, Tebu, France) at 4° C. overnight. Each membrane was rinsed three times with TSB-T buffer, and was then incubated at ambient temperature for 2 h with a horseradish peroxidase-coupled anti-rabbit immunoglobulin antibody (Molecular Probes). Each membrane was rinsed four times with TBS-T buffer and the reaction was visualized using the ECL chemiluminescence kit (Amersham Pharmacia Biotech) with X-Omat AR film from Kodak.

Here again, as represented in FIG. 1B, NGF was detected with the cancerous cells and the submaxillary gland (band at 14 kDa), whereas this band was absent for the non-cancerous cells.

This result confirms that of example 1.

EXAMPLE 3

Demonstration of the Expression of NGF in Breast Cancer Cells by ELISA 3.1 Cells Tested The cells tested are those indicated in point 1.1. above.

3.2 ELISA

For this assay, a two-site assay for human β-NGF was used. In summary, immunoplates were coated with 1 μg/ml of monoclonal capture antibody (R&D Systems, UK) diluted in a diluting buffer (0.1% BSA, 0.005% Tween 20 in a saline solution buffered with Tris, pH 7.3). The control wells were coated with the same amount of mouse IgG (R&D Systems). Each well received 100 μl of this dilution and the plates were sealed and incubated at ambient temperature overnight.

The wells were washed three times with 400 μl of PBS, pH 7.4, containing 0.05% of Tween 20. The plates were then blocked at ambient temperature using 1% of bovine serum albumin, 5% of sucrose and 0.005% of $NaN_3$ in the same buffer.

After 2 h, each well was washed, dilutions of unknown and standard products in a volume of 100 μl were added, and the plates were re-covered with an adhesive tape and were incubated at ambient temperature overnight.

Human β-NGF (R&D Systems) was used as a standard sample, in a proportion of 0.25 to 8 ng/ml in 100 μl of diluting buffer.

The plates were then washed thoroughly and the specific anti-human β-NGF goat IgG detection antibody (BAF-256, R&D Systems) was added in a proportion of 50 ng/ml, before incubation for 2 h at ambient temperature.

After incubation, the immunoplates were washed three times with washing buffer and 100 μl of streptavidin/horseradish peroxidase were added for a 20 min incubation at ambient temperature.

The reaction began with the addition of 100 μl of a substrate solution for a 30 min incubation at ambient temperature and in the dark.

After this period, 50 μl of a stop solution (1M $H_2SO_4$) were added to each well. The optical density was determined in 30 min, using a microplate reader assembly at 595 or 450 nm.

The optical density results (mean after three independent assays) are given in FIG. 1C. They demonstrate a similar level of NGF in all the breast cancer cell lines tested.

EXAMPLE 4

Culturing of NGF-Sensitive Cells

To do this, cells which develop in the presence of NGF, i.e. PC12 cells, were cocultured with MCF-7 breast cancer cells, as described in point 1.1 above, or else with NBEC cells, as described in point 1.1 above, as a control.

The PC12 cells were cultured beforehand at 37° C. in a 5% $CO_2$ atmosphere, in Dulbecco's modified minimum essential medium (DMEM) supplemented with 3 g/l of sodium bicarbonate, 4 mM of L-glutamine, 10% of fetal calf serum, 5% of horse serum and 100 units/ml of penicillin/streptomycin.

The coculturing was carried out with Transwell® tissue culture-treated polycarbonate plates (12 mm in diameter and 12 μm pore size). An initial equilibrating period was observed by adding the media to the central well of the plate, and then to the Transwell® insert, which operation was followed by incubation at 37° C. for 3 h.

The PC12 cells were seeded in 12-well plates coated with collagen for 24 h in order to ensure correct attachment to the culture plates. The MCF-7 or NCBE cells were seeded inside the Transwell® insert, corresponding to the upper compartment, in the complete medium for 24 h.

After this time, each cell line was rinsed three times with serum-free medium and was incubated in a withdrawal medium. In the control experiments, the medium was supplemented with medium containing either NGF, or an inhibitor of tyrosine kinase trk activity (K-252-a, Calbiochem, France), or anti-human β-NGF mouse monoclonal antibody (MAB-256, R&D Systems).

The coculturing was carried out for 48 h. After this period, the PC12 cells were fixed with cold methanol (−20° C.) for 20 min and then washed with a phosphate buffered saline (PBS) solution before assembly with cover slips and Glycergel (Dako, France).

The percentage of cells bearing neurites, defined as cells with one or more neurite extensions twice the length of the cell body, was counted. Photomicrographs were also taken using a phase-contrast microscope equipped with an Olympus optical digital camera.

The results are given in FIG. 2, in which:

FIG. 2A shows the experimental scheme where (2) corresponds to the cancerous or non-cancerous cells and (1) corresponds to the PC12 cells, FIG. 2B provides photographs where:

photographs 2 and 3 show the culture of PC12 cells as a control, respectively without NGF and in the presence of NGF, where neurite development due to differentiation is observed, photograph 4, which relates to the coculture of MCF-7 and PC12 cells, shows that the PC12 cells are differentiated after 48 h of culture, photograph 5, which relates to the coculture of MCF-7 and PC12 cells in the presence of the anti-NGF antibody, shows a strong inhibition of the PC12 cell differentiation due to the antibody, photograph 6, which relates to the coculture of MCF-7 and PC12 cells in the presence of the inhibitor K-252a, shows a strong inhibition of the PC12 cell differentiation due to the inhibitor, and photograph 7, which relates to the coculture of normal NBEC cells and PC12 cells, demonstrates the absence of PC12 cell differentiation.

EXAMPLE 5

Immunohisochemistry for the Detection of NGF in Breast Cancer Biopsies 5.1 Sampling and Fixing of Biopsies Immediately after operation, the biopsies of human breast cancer tissue or of non-cancerous normal tissue (control) were fixed with a 10% formol solution for 24 hours. After dehydration with increasing alcohol baths (30 to 100%), the samples were embedded in paraffin. Sections were cut on a microtome (thin section of 5 micrometers), and then fixed on slides coated with 3-aminopropyltriethoxysilane (TESPA, Dako, France).

5.2 Deparaffining of Slides

The slides were deparaffined by soaking them in baths according to the following procedure:

2 baths of toluene (10 min), 1 bath of 100% alcohol (10 min), 1 bath of 95% alcohol (10 min), 1 bath of 70% alcohol (10 min), 1 bath of water (10 min).

The slides were then stored at +4° C.

5.3 NGF Labeling

The sections were rinsed with TBS-0.1% Tween (TBS: 17.54 g of NaCl, 2.42 g of Trisbase, qs 2 liters of water, pH 7.4) for 10 min with agitation. The antigens were reactivated with 0.01M citrate buffer (1.05 g of citric acid monohydrate, qs 500 ml of distilled water, pH 6 (NaOH)) for 2 times 5 min in a water bath at 95° C. The slides were incubated for 5 min with agitation in 3% aqueous hydrogen peroxide/TBS. The slides were saturated for one hour at ambient temperature in TBS/3% BSA.

The slides were then incubated for 2 h at ambient temperature in a humid chamber with 80 μl of anti-NGF primary antibodies (Santa Cruz, Tebu, France), diluted to 1/50 in TBS/3% BSA. They were washed 3 times in TBS/Tween for 5 min with agitation.

The slides were then incubated again, for 2 h at ambient temperature in a humid chamber with 80 μl of anti-rabbit IgG monkey secondary antibody, said antibody having been bound to horseradish peroxidase (Jackson Laboratories, US), diluted to 1/100 in TBS/3% BSA.

The slides were washed three times in TBS/Tween for 5 min with agitation, rinsed three times with PBS for 5 min with agitation, dried, and then incubated for 10 min with 100 μl of DAB (sigma fast 3,3-diaminobenzidine; 1 DAB tablet+1 $H_2O_2$/urea tablet in 1 ml of water).

The staining was verified under a microscope and stopped in a bath of PBS. A counter-staining was performed in order to visualize the mammary structures, by immersing in Harris hematoxylin in modified solution (Sigma) for 4 s. Rinsing was carried out in alkaline water and then in a bath of PBS.

The slide was mounted on glycergel heated in a 50° C. water bath.

The slides were photographed by means of a binocular magnifying lens (Zeiss).

The photographs of immunohistochemistry on the sections thus obtained are represented in FIG. 3. Photographs A and B relate to the normal tissue, respectively with or without NGF labeling. Photographs C to F relate to the cancerous tissue, photographs C and E relate to the sections without NGF labeling (negative control) and photographs D and F relate to the sections with NGF labeling. The size bar represents 250 micrometers for photographs A, B, E and F or 600 micrometers for photographs C and D.

The results clearly show that NGF is detected by immunohistochemistry on biopsy slides, in the breast cancer epithelial cells, but not in the normal mammary epithelial cells (epithelial cells labeled with the anti-NGF antibody, and as a result stained, in the tumoral mammary glands in D and F compared with C and E, and not in the normal mammary glands in B compared with A).

EXAMPLE 6

Detection of NGF in the Tumor Cells by Flow Cytometry

The MCF-7 cells were detached by scraping the bottom of the culture dish. 100 μl of fixer (Coulter) were then added, with incubation for 15 minutes at ambient temperature. The cells were then washed three times with PBS and centrifuged at 1900 rpm for 5 minutes.

100 μl of permeabilizer (Coulter) were added, and then incubation was carried out for 5 minutes at ambient temperature.

20 μl of the unlabeled anti-NGF mouse monoclonal antibody (R&D Systems, diluted to 1/100) were added and then incubation was carried out for 15 minutes at ambient temperature.

The cells were then washed three times with PBS and centrifuged at 1900 rpm for 5 minutes.

20 μl of the FITC-labeled anti-mouse 2nd antibody (R&D Systems, diluted to 1/50) were added and then incubation was carried out for 15 minutes at ambient temperature and in the dark.

The cells were then washed three times with PBS and centrifuged at 1900 rpm for 5 minutes.

The cells were taken up in 500 μl of PBS and then the reading was performed with a flow cytometer (Beckman Coulter® EPICS®).

The results obtained show that more than 30% of the cells of this cell line contain intracytoplasmic NGF.

Such a method is applicable with tumor cells isolated from a biological sample.

EXAMPLE 7

Influence of an Anti-NGF Antibody and of a Pharmacological Inhibitor on the Growth of the Cancer Cells The effect of the blocking antibody MAB-256 (above) and of the inhibitor K-252a on the growth of MCF-7 cells was studied. To do this, the cells were seeded in a proportion of $2\times10^4$ cells/ml in 35 mm dishes in complete medium. After having reached 40% confluency, the cells were washed twice and were left without nutrients in a serum-free medium containing fibronectin (2 μg/ml) and transferrin (30 μg/ml) for 3 h. The following hour, the medium was replaced with 2 ml of the same medium containing the inhibitor K-252a or the antibody MAB-26 at various concentrations in order to study the effect of the pharmacological inhibitor or of the blocking inhibitor on the base line growth level.

After treatment for 24, 36, 48 and 72 h, the number of cells was determined, after trypsinization of the monolayer culture with a solution of 0.25% trypsin/EDTA, using a hemocytometer.

An anti-mouse monoclonal antibody (A4700, Sigma), i.e. an irrelevant antibody, was also used in order to determine the specificity of the blocking antibody.

The results are given in FIG. 4, in which:

FIG. 4A shows that the growth of the MCF-7 cells in basic medium (squares) decreases in the presence of antibody (triangles) and of inhibitor (diamonds).

FIGS. 4B and 4C show that there is a dose effect of the antibody and of the inhibitor, respectively, on the proliferative effect of NGF for the cancerous cells.

NGF can therefore indeed be used as a therapeutic target.

EXAMPLE 8

Effect of Anti-NGF Antibodies on Mammary Cell Tumorigenesis In Vivo

MDA-MB-231 breast cancer cell growth was studied as follows:

30 SCID (Severe Combined Immuno-Deficiency) mice were given a subcutaneous injection into the flank, at time 0 (D0) of $3\times10^6$ MDA-MB-231 cells, derived from in vitro cultures, in 50 microliters of PBS per mouse. The mice were kept under standard breeding colony conditions at ambient temperature, with day/night alternation and unlimited access to food and drink.

Fourteen, 21 and 28 days after injection of the cells, half the mice were injected with anti-human NGF blocking antibodies (Oncogene Research Product, VWR France) at the periphery of the tumor (subcutaneous in the flank, 1 cm from the point of injection of the tumor cells), at the concentration of 12.5 micrograms in 50 microliters of PBS buffer per mouse.

The tumor size was measured on the living mice, treated with the anti-NGF antibody or not treated, using an electronic slide gauge, 21 and 35 days after the injection of the cancer cells (D21 and D35, respectively). The volume of the tumor was calculated with the following formula: 0.5236×length (mm)×width (mm)×(length+width)/2.

The weight of the tumors at D35 was also measured on these same mice, after the animal had been sacrificed, using an electronic precision balance.

Finally, the number of metastases in their liver was counted macroscopically.

Figure 3:
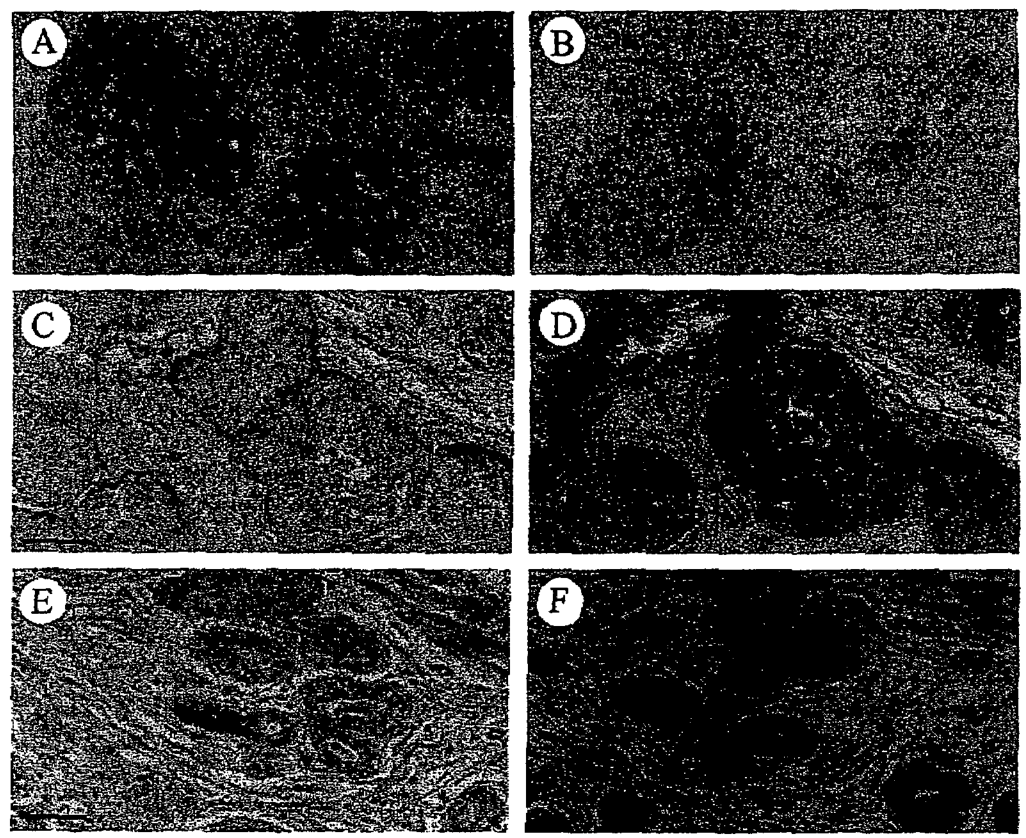
Figure 5:
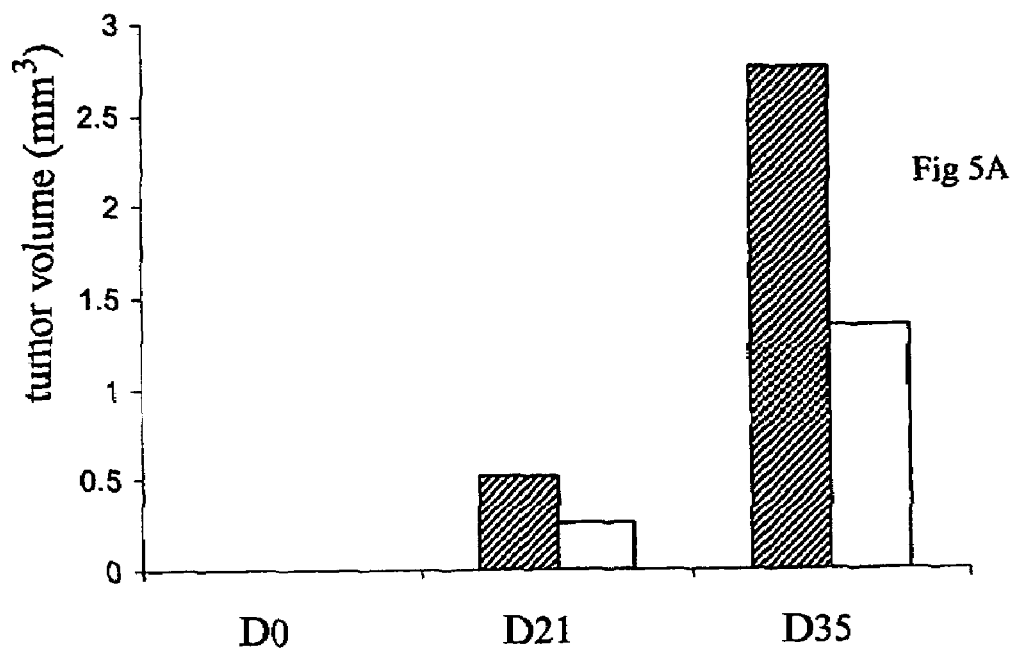
Figure 5:
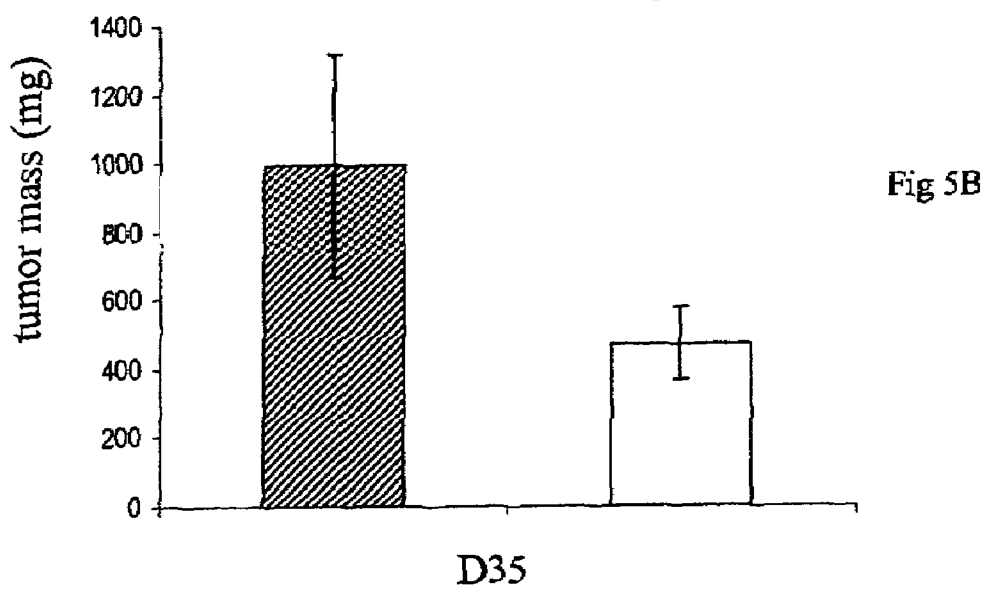
Figures 5, 5C:
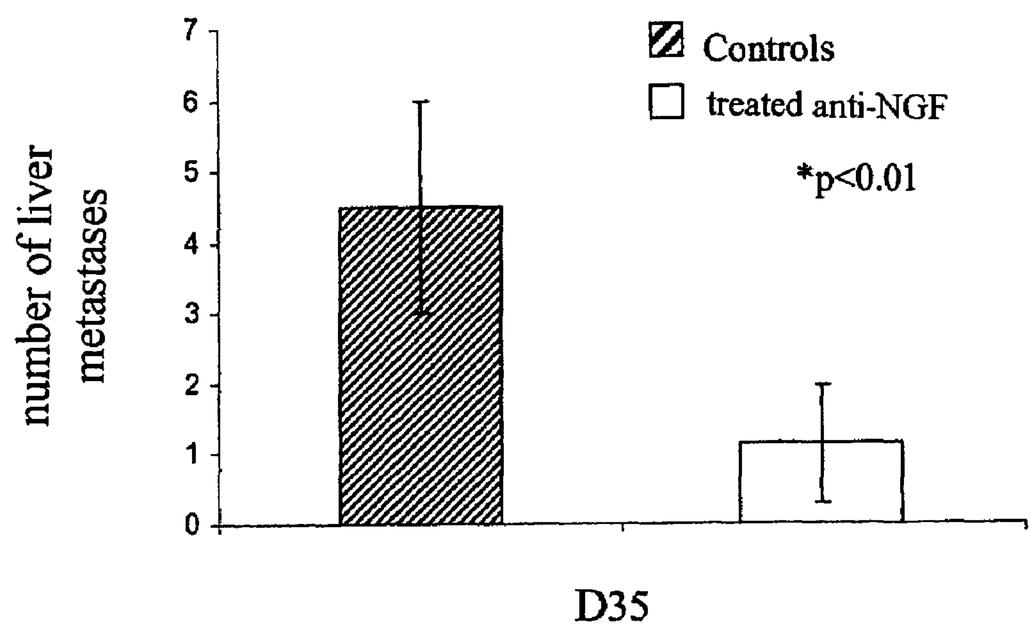

The respective results of the measurements above (mean) are given on the graphs in FIG. 5, where the lined histogram corresponds to the mice not treated with the anti-NGF antibody (controls) and the histogram not filled in corresponds to the mice treated with said antibody.

These graphs demonstrate that the treatments with an anti-NGF result in a decrease in the tumor mass and volume, and also in the number of metastases in the case of breast cancer.

---

The invention claimed is:

1. A method for the in vitro diagnosis of breast cancer, comprising determining the presence, in a biological sample obtained from a patient suspected of suffering from breast cancer, of Nerve Growth Factor (NGF) that has been secreted by breast cancer tissue;

wherein the biological sample is blood.

2. The method as claimed in claim 1, wherein the presence of NGF is demonstrated by direct detection of NGF in said biological sample.

3. The method as claimed in claim 2, wherein the detection of NGF is carried out by an immunoassay or by mass spectrometry.

4. The method as claimed in claim 1, wherein the detection of NGF further comprises culturing NGF-sensitive cells in the presence of said biological sample.

5. A method for the early diagnosis, screening, therapeutic follow-up and diagnosis of relapse in the case of breast cancer, comprising determining the presence, in a biological sample obtained from a patient who has been treated for breast cancer, of Nerve Growth Factor (NGF) that has been secreted by breast cancer tissue;

wherein the biological sample is blood.

6. The method as claimed in claim 1, wherein the presence of the secreted NGF is demonstrated by indirect detection, in said biological sample, of the NGF.

7. The method as claimed in claim 6, wherein the indirect detection, in the biological sample, of the NGF that has been secreted by breast cancer tissue is carried out by the use of a ligand and an anti-ligand, wherein the ligand binds to the NGF.

8. The method according to claim 1, wherein the biological sample does not contain breast cancer cells.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: sense probe

<400> SEQUENCE: 1

gacagtgtca gcgtgtgggt t                                              21


<210> SEQ ID NO 2
```

-continued

```
<211> LENGTH: 20
<212> TYPE: DNA
<213> ORGANISM: Artificial Sequence
<220> FEATURE:
<223> OTHER INFORMATION: antisense probe

<400> SEQUENCE: 2

cccaacacca tcacctcctt                                                  20
```